US006458358B1

(12) United States Patent
Timoney et al.

(10) Patent No.: US 6,458,358 B1
(45) Date of Patent: Oct. 1, 2002

(54) **COMPOUNDS ENCODING THE PROTECTIVE M-LIKE PROTEIN OF *STREPTOCOCCUS EQUI* AND ASSAYS THEREFOR**

(75) Inventors: John F. Timoney, Lexington, KY (US); Sergey Artiushin, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/103,664

(22) Filed: Jun. 23, 1998

Related U.S. Application Data

(60) Provisional application No. 60/050,577, filed on Jun. 24, 1997.

(51) Int. Cl.[7] ........................ A61K 39/02; A61K 39/00; A61K 39/385; A61K 39/116; A61K 45/00

(52) U.S. Cl. ................................ 424/190.1; 424/192.1; 424/193.1; 424/203.1; 424/283.1; 530/350; 514/12

(58) Field of Search ........................... 424/184.1, 190.1, 424/185.1, 192.1, 193.1, 203.1, 283.1; 530/300, 350, 403, 825; 536/23.1; 435/320.1; 514/12

(56) References Cited

U.S. PATENT DOCUMENTS

| | | | |
|---|---|---|---|
| 4,877,612 A | * | 10/1989 | Berger et al. |
| 5,183,659 A | | 2/1993 | Timoney |
| 5,204,098 A | * | 4/1993 | Szu et al. |

FOREIGN PATENT DOCUMENTS

| | | |
|---|---|---|
| WO | WO 98/01561 | 1/1998 |

OTHER PUBLICATIONS

Wittmann–Liebold et al., FEBS Lttrs., 121(1):105–112, 1980.*

Lee et al., WO9505392, Feb. 23, 1995.*

Alving et al., Progress in Clin. & Biol. Res., 47:339–55, 1980.*

Stites et al., Basic and Clinical Immunology, Appleton & Lange, pp. 101–108, 1991.*

WO8909064, Fishchetti, and alignment P90955, Geneseq 36, Oct. 5, 1989.*

Benjamini, Immunology A short course, Wiley Liss, p. 4 and 392, 1991.*

Harlow & Lane, Cold Spring Harbor Labs, 1988.*

Boschwitz and Timoney, 17 *Microbiol. Pathogenesis* 121 (1994).

Boschwitz and Timoney, 62 *Infect. Immun.* 3515 (1994).

Debs, et al., 265 *J. Biol. Chem.* 10189 (1990).

Lancefield and Perlmann, 96 *J. Exp. Med.* 71 (1952).

Galán and Timoney, 26 *J. Clin. Microbiol.* 1142 (1988).

Pycock, et al., 42 *Res. Vet. Sci.* 411 (1987).

* cited by examiner

*Primary Examiner*—Gary L. Kunz
*Assistant Examiner*—Sharon Turner
(74) *Attorney, Agent, or Firm*—McDermott, Will & Emery

(57) ABSTRACT

The present invention relates generally to molecular compounds which encode the protective M-like protein of *Streptococcus equi* (SeM), the amino acid compound which is thereby encoded, and compositions of matter which incorporate either the encoding compounds or the cellular components for which they encode. For instance, vaccines which utilize the amino acid compounds or vectors and cell lines useful to make the amino acid compounds described herein are subjects of the present invention. The present invention provides methods to stimulate *S. equi*-specific immune response in horses. It also provides diagnostic assays for *Streptococcus equi.*

6 Claims, 6 Drawing Sheets

```
                                              -35
1    TACATTCTTGCTTATTAAATAAAAATGACAATGTACTGCATAAAGAAGTTCCTGTCATTA
     -10
61   AAATAAAAGTGCCATGAGGTTATAATAGTATGGTAAAACAAAAAAGTGTGCCCATAACGG
1       RBS          M  F  L  R  N  N  K  P  K  F  S  I  R  K
121  GTACAGAGGAATTGACATATGTTTTTGAGAAATAACAAGCCAAAATTTAGCATCAGAAAA
15    L  S  A  G  A  A  S  V  L  V  A  T  S  V  L  G  G  T  T  V
181  CTAAGTGCCGGTGCAGCATCAGTATTAGTTGCAACAAGTGTGTTGGGAGGGACAACTGTA
35    K  A  N  S  E  V  S  R  T  A  T  P  R  L  S  R  D  L  K  N
241  AAAGCGAACTCTGAGGTTAGTCGTACGGCGACTCCAAGATTATCGCGTGATTTAAAAAAT
55    R  L  S  D  I  A  I  S  G  D  A  S  S  A  Q  K  V  R  N  L
301  AGATTAAGCGATATAGCCATAAGTGGAGATGCCTCATCAGCCCAAAAAGTTCGAAATCTT
75    L  K  G  A  S  V  G  D  L  Q  A  L  L  R  G  L  D  S  A  R
361  CTAAAAGGCGCCTCTGTTGGGGATTTACAGGCATTATTGAGAGGTCTTGATTCAGCAAGG
95    A  A  Y  G  R  D  D  Y  Y  N  L  L  M  H  L  S  S  M  L  N
421  GCTGCGTATGGTAGAGATGATTATTACAATTTATTGATGCACCTTTCATCGATGTTAAAT
115   D  K  P  D  G  D  R  R  Q  L  S  L  A  S  L  L  V  D  E  I
481  GATAAACCTGATGGGGATAGAAGACAATTAAGTTTGGCTTCATTACTTGTAGATGAAATT
135   E  K  R  I  A  D  G  D  R  Y  A  K  L  L  E  A  K  L  A  A
541  GAAAAGCGGATTGCTGATGGAGATAGGTATGCAAAACTTCTTGAGGCTAAACTTGCAGCT
155   I  K  S  Q  Q  E  M  L  R  E  R  D  S  Q  L  R  N  L  E  K
601  ATTAAATCTCAACAAGAAATGCTTAGAGAAAGAGATTCCCAACTTCGAAATCTAGAGAAG
175   E  K  E  Q  E  L  T  K  A  K  D  E  R  Q  A  L  T  E  S  F
661  GAGAAAGAACAAGAGCTCACAAAAGCTAAAGATGAGCGTCAAGCTCTTACCGAATCATTC
195   N  K  T  L  S  R  S  T  K  E  Y  N  K  L  K  T  E  L  A  K
721  AACAAAACTTTATCAAGATCAACAAAAGAGTATAATAAACTAAAAACAGAACTTGCAAAA
215   E  K  E  K  A  A  K  M  T  K  E  L  A  D  K  L  S  N  A  E
781  GAAAAAGAAAAAGCAGCTAAGATGACTAAGGAATTAGCAGATAAGCTAAGCAATGCTGAA
235   A  S  R  D  K  A  F  A  V  S  K  D  L  A  D  K  L  S  S  A
841  GCAAGTCGTGATAAAGCCTTTGCAGTATCAAAAGATTTAGCAGATAAACTAAGTAGTGCT
255   E  A  S  R  D  K  A  F  A  V  S  K  D  L  A  D  K  L  A  A
901  GAAGCAAGTCGTGATAAAGCTTTTGCAGTATCAAAAGATTTAGCAGATAAATTGGCAGCT
275   K  T  A  E  A  E  K  L  M  E  N  V  G  S  L  D  R  L  V  E
961  AAAACAGCAGAAGCTGAAAAGTTAATGGAAAACGTTGGTAGTCTAGACCGCTTGGTAGAG
295   S  A  K  R  E  M  A  Q  K  L  A  E  I  D  Q  L  T  A  D  K
1021 TCTGCAAAACGTGAAATGGCTCAAAAATTAGCAGAAATTGATCAATTAACTGCTGATAAG
315   A  K  A  D  A  E  L  A  A  A  N  D  T  I  A  S  L  Q  T  E
1081 GCTAAGGCTGATGCAGAGCTTGCAGCTGCAAATGACACCATTGCATCACTTCAAACAGAG
335   L  E  K  A  K  T  E  L  A  V  S  E  R  L  I  E  S  G  K  R
1141 CTAGAAAAAGCTAAGACAGAGCTTGCTGTTTCAGAGCGTTTGATTGAATCAGGCAAACGT
355   E  I  A  E  L  Q  K  Q  K  D  A  S  D  K  A  L  V  E  S  Q
1201 GAAATTGCTGAGCTACAAAAACAAAAAGATGCTTCTGATAAGGCTTTAGTAGAATCACAA
375   A  N  V  A  E  L  E  K  Q  K  A  A  S  D  A  K  V  A  E  L
1261 GCTAATGTAGCAGAGCTTGAAAAACAAAAAGCAGCATCAGATGCTAAGGTAGCAGAGCTT
395   E  K  E  V  E  A  A  K  A  E  V  A  D  L  K  A  Q  L  A  K
1321 GAAAAAGAAGTTGAAGCTGCTAAAGCTGAGGTTGCAGATCTTAAAGCACAATTAGCTAAG
415   K  E  E  E  L  E  A  V  K  K  E  K  E  A  L  E  A  K  I  E
1381 AAAGAAGAAGAGCTTGAAGCCGTTAAGAAGGAAAAAGAAGCGCTTGAAGCTAAGATTGAA
435   E  L  K  K  A  H  A  E  E  L  S  K  L  K  E  M  L  E  K  K
```

FIG. 1A

```
1441  GAGCTCAAAAAAGCTCATGCTGAGGAACTTTCAAAACTTAAAGAAATGCTTGAGAAGAAA
 455   D  H  A  N  A  D  L  Q  A  E  I  N  R  L  K  Q  E  L  A  D
1501  GACCATGCAAATGCAGATCTTCAAGCAGAAATCAATCGCTTGAAGCAAGAGCTAGCTGAC
 475   R  I  K  S  L  S  Q  G  G  R  A  S  Q  T  N  P  G  T  T  T
1561  AGGATTAAGTCATTGTCACAAGGTGGTCGTGCTTCACAAACAAACCCAGGCACTACAACT
 495   A  K  A  G  Q  L  P  S  T  G  E  S  A  N  P  F  F  T  I  A
1621  GCTAAAGCAGGTCAATTGCCATCTACTGGTGAGTCTGCTAACCCATTCTTCACTATTGCA
 515   A  L  T  V  I  A  G  A  G  M  A  V  V  S  P  K  R  K  E  N
1681  GCTCTTACTGTCATCGCTGGTGCTGGAATGGCTGTGGTGTCTCCTAAACGCAAAGAAAAC

1741  TAAGCTATTTCCTCTTTCCCCAATGGACAATAGCCGAAATAATAGAGCGACTATCGTTCT
                     terminator
1801  AACACAAAAGCAACAGTCTCCTGTCTGTTGCTTTTTGTGATATTAGGGCTCATCAGTCTA

1861  GGCTAATGGTTTTCTGCGCTTTATCTGCA
```

(SEQ ID NO:10)

FIG. 1B

SEQUENCE LISTING

```
<160> NUMBER OF SEQ ID NOS: 10

<210> SEQ ID NO 1
<211> LENGTH: 2091
<212> TYPE: DNA
<213> ORGANISM: Streptococcus equi

<400> SEQUENCE: 1

agctttctgt cacctgatgg tccttatcaa atactgtaat tgataacttc aaacagccct      60

gtagagattt tactaacgac atagtatcca tgctaagcgt caccccccttc ataatcctca    120

cggtatctta ttctatctta aaatttaaga aaagcaagga tatgcactta taatgaaaaa     180

atagacataa aaaacaataa tatacattct tgcttattaa ataaaaatga caatgtactg     240

cataaagaag ttcctgtcat taaaataaaa gtgccatgag gttataatag tatggtaaaa     300

caaaaaagtg tgcccataac gggtagagag gaattgacat atgtttttga gaaataacaa     360

gccaaaattt agcatcagaa aactaagtgc cggtgcagca tcagtattag ttgcaacaag     420

tgtgttggga gggacaactg taaaagcgaa ctctgaggtt agtcgtacgg cgactccaag     480

attatcgcgt gatttaaaaa atagattaag cgatatagcc ataagtggag atgcctcatc     540

agcccaaaaa gttcgaaatc ttctaaaagg cgcctctgtt ggggatttac aggcattatt     600

gagaggtctt gattcagcaa gggctgcgta tggtagagat gattattaca atttattgat     660

gcacctttca tcgatgttaa atgataaacc tgatggggat agaagacaat taagtttggc     720

ttcattactt gtagatgaaa ttgaaaagcg gattgctgat ggagataggt atgcaaaact     780

tcttgaggct aaacttgcag ctattaaatc tcaacaagaa atgcttagag aaagagattc     840

ccaacttcga aatctagaga aggagaaaga acaagagctc acaaaagcta aagatgagcg     900

tcaagctctt accgaatcat tcaacaaaac tttatcaaga tcaacaaaag agtataataa     960

actaaaaaca gaacttgcaa aagaaaaaga aaaagcagct aagatgacta aggaattagc    1020

agataagcta agcaatgctg aagcaagtcg tgataaagcc tttgcagtat caaaagattt    1080

agcagataaa ctaagtagtg ctgaagcaag tcgtgataaa gcttttgcag tatcaaaaga    1140

tttagcagat aaattggcag ctaaaacagc agaagctgaa aagttaatgg aaaacgttgg    1200

tagtctagac cgcttggtag agtctgcaaa acgtgaaatg gctcaaaaat tagcagaaat    1260
```

-continued

```
tgatcaatta actgctgata aggctaaggc tgatgcagag cttgcagctg caaatgacac   1320

cattgcatca cttcaaacag agctagaaaa agctaagaca gagcttgctg tttcagagcg   1380

tttgattgaa tcaggcaaac gtgaaattgc tgagctacaa aaacaaaaag atgcttctga   1440

taaggcttta gtagaatcac aagctaatgt agcagagctt gaaaaacaaa aagcagcatc   1500

agatgctaag gtagcagagc ttgaaaaaga agttgaagct gctaaagctg aggttgcaga   1560

tcttaaagca caattagcta agaaagaaga agagcttgaa gccgttaaga aggaaaaaga   1620

agcgcttgaa gctaagattg aagagctcaa aaaagctcat gctgaggaac tttcaaaact   1680

taaagaaatg cttgagaaga aagaccatgc aaatgcagat cttcaagcag aaatcaatcg   1740

cttgaagcaa gagctagctg acaggattaa gtcattgtca caaggtggtc gtgcttcaca   1800

aacaaaccca ggcactacaa ctgctaaagc aggtcaattg ccatctactg gtgagtctgc   1860

taacccattc ttcactattg cagctcttac tgtcatcgct ggtgctggaa tggctgtggt   1920

gtctcctaaa cgcaaagaaa actaagctat ttcctctttc cccaatggac aatagccgaa   1980

ataatagagc gactatcgtt ctaacacaaa agcaacagtc tcctgtctgt tgctttttgt   2040

gatattaggg ctcatcagtc taggctaatg gttttctgcg ctttatctgc a            2091


<210> SEQ ID NO 2
<211> LENGTH: 534
<212> TYPE: PRT
<213> ORGANISM: Streptococcus equi

<400> SEQUENCE: 2

Met Phe Leu Arg Asn Asn Lys Pro Lys Phe Ser Ile Arg Lys Leu Ser
1               5                   10                  15

Ala Gly Ala Ala Ser Val Leu Val Ala Thr Ser Val Leu Gly Gly Thr
            20                  25                  30

Thr Val Lys Ala Asn Ser Glu Val Ser Arg Thr Ala Thr Pro Arg Leu
        35                  40                  45

Ser Arg Asp Leu Lys Asn Arg Leu Ser Asp Ile Ala Ile Ser Gly Asp
    50                  55                  60

Ala Ser Ser Ala Gln Lys Val Arg Asn Leu Leu Lys Gly Ala Ser Val
65                  70                  75                  80

Gly Asp Leu Gln Ala Leu Leu Arg Gly Leu Asp Ser Ala Arg Ala Ala
                85                  90                  95

Tyr Gly Arg Asp Asp Tyr Tyr Asn Leu Leu Met His Leu Ser Ser Met
            100                 105                 110

Leu Asn Asp Lys Pro Asp Gly Asp Arg Arg Gln Leu Ser Leu Ala Ser
        115                 120                 125

Leu Leu Val Asp Glu Ile Glu Lys Arg Ile Ala Asp Gly Asp Arg Tyr
    130                 135                 140

Ala Lys Leu Leu Glu Ala Lys Leu Ala Ala Ile Lys Ser Gln Gln Glu
145                 150                 155                 160

Met Leu Arg Glu Arg Asp Ser Gln Leu Arg Asn Leu Glu Lys Glu Lys
                165                 170                 175

Glu Gln Glu Leu Thr Lys Ala Lys Asp Glu Arg Gln Ala Leu Thr Glu
            180                 185                 190

Ser Phe Asn Lys Thr Leu Ser Arg Ser Thr Lys Glu Tyr Asn Lys Leu
        195                 200                 205

Lys Thr Glu Leu Ala Lys Glu Lys Glu Lys Ala Ala Lys Met Thr Lys
    210                 215                 220

Glu Leu Ala Asp Lys Leu Ser Asn Ala Glu Ala Ser Arg Asp Lys Ala
```

-continued

```
225                 230                 235                 240

Phe Ala Val Ser Lys Asp Leu Ala Asp Lys Leu Ser Ser Ala Glu Ala
                245                 250                 255

Ser Arg Asp Lys Ala Phe Ala Val Ser Lys Asp Leu Ala Asp Lys Leu
            260                 265                 270

Ala Ala Lys Thr Ala Glu Ala Glu Lys Leu Met Glu Asn Val Gly Ser
        275                 280                 285

Leu Asp Arg Leu Val Glu Ser Ala Lys Arg Glu Met Ala Gln Lys Leu
    290                 295                 300

Ala Glu Ile Asp Gln Leu Thr Ala Asp Lys Ala Lys Ala Asp Ala Glu
305                 310                 315                 320

Leu Ala Ala Ala Asn Asp Thr Ile Ala Ser Leu Gln Thr Glu Leu Glu
                325                 330                 335

Lys Ala Lys Thr Glu Leu Ala Val Ser Glu Arg Leu Ile Glu Ser Gly
            340                 345                 350

Lys Arg Glu Ile Ala Glu Leu Gln Lys Gln Lys Asp Ala Ser Asp Lys
        355                 360                 365

Ala Leu Val Glu Ser Gln Ala Asn Val Ala Glu Leu Glu Lys Gln Lys
    370                 375                 380

Ala Ala Ser Asp Ala Lys Val Ala Glu Leu Glu Lys Glu Val Glu Ala
385                 390                 395                 400

Ala Lys Ala Glu Val Ala Asp Leu Lys Ala Gln Leu Ala Lys Lys Glu
                405                 410                 415

Glu Glu Leu Glu Ala Val Lys Lys Glu Lys Glu Ala Leu Glu Ala Lys
            420                 425                 430

Ile Glu Glu Leu Lys Lys Ala His Ala Glu Glu Leu Ser Lys Leu Lys
        435                 440                 445

Glu Met Leu Glu Lys Lys Asp His Ala Asn Ala Asp Leu Gln Ala Glu
    450                 455                 460

Ile Asn Arg Leu Lys Gln Glu Leu Ala Asp Arg Ile Lys Ser Leu Ser
465                 470                 475                 480

Gln Gly Gly Arg Ala Ser Gln Thr Asn Pro Gly Thr Thr Thr Ala Lys
                485                 490                 495

Ala Gly Gln Leu Pro Ser Thr Gly Glu Ser Ala Asn Pro Phe Phe Thr
            500                 505                 510

Ile Ala Ala Leu Thr Val Ile Ala Gly Ala Gly Met Ala Val Val Ser
        515                 520                 525

Pro Lys Arg Lys Glu Asn
    530
```

<210> SEQ ID NO 3
<211> LENGTH: 1603
<212> TYPE: DNA
<213> ORGANISM: Streptococcus equi

<400> SEQUENCE: 3

```
atgtttttga gaaataacaa gccaaaattt agcatcagaa aactaagtgc cggtgcagca     60

tcagtattag ttgcaacaag tgtgttggga gggacaactg taaaagcgaa ctctgaggtt    120

agtcgtacgg cgactccaag attatcgcgt gatttaaaaa atagattaag cgatatagcc    180

ataagtggag atgcctcatc agcccaaaaa gttcgaaatc ttctaaaagg cgcctctgtt    240

ggggatttac aggcattatt gagaggtctt gattcagcaa gggctgcgta tggtagagat    300

gattattaca atttattgat gcacctttca tcgatgttaa atgataaacc tgatggggat    360
```

-continued

```
agaagacaat taagtttggc ttcattactt gtagatgaaa ttgaaaagcg gattgctgat    420

ggagataggt atgcaaaact tcttgaggct aaacttgcag ctattaaatc tcaacaagaa    480

atgcttagag aaagagattc ccaacttcga aatctagaga aggagaaaga acaagagctc    540

acaaaagcta aagatgagcg tcaagctctt accgaatcat tcaacaaaac tttatcaaga    600

tcaacaaaag agtataataa actaaaaaca gaacttgcaa aagaaaaaga aaaagcagct    660

aagatgacta aggaattagc agataagcta agcaatgctg aagcaagtcg tgataaagcc    720

tttgcagtat caaaagattt agcagataaa ctaagtagtg ctgaagcaag tcgtgataaa    780

gcttttgcag tatcaaaaga tttagcagat aaattggcag ctaaaacagc agaagctgaa    840

aagttaatgg aaaacgttgg tagtctagac cgcttggtag agtctgcaaa acgtgaaatg    900

gctcaaaaat tagcagaaat tgatcaatta actgctgata aggctaaggc tgatgcagag    960

cttgcagctg caaatgacac cattgcatca cttcaaacag agctagaaaa agctaagaca   1020

gagcttgctg tttcagagcg tttgattgaa tcaggcaaac gtgaaattgc tgagctacaa   1080

aaacaaaaag atgcttctga taaggcttta gtagaatcac aagctaatgt agcagagctt   1140

gaaaaacaaa aagcagcatc agatgctaag gtagcagagc ttgaaaaaga agttgaagct   1200

gctaaagctg aggttgcaga tcttaaagca caattagcta agaaagaaga agagcttgaa   1260

gccgttaaga aggaaaaaga agcgcttgaa gctaagattg aagagctcaa aaaagctcat   1320

gctgaggaac tttcaaaact taaagaaatg cttgagaaga aagaccatgc aaatgcagat   1380

cttcaagcag aaatcaatcg cttgaagcaa gagctagctg acaggattaa gtcattgtca   1440

caaggtggtc gtgcttcaca aacaaaccca ggcactacaa ctgctaaagc aggtcaattg   1500

ccatctactg gtgagtctgc taacccattc ttcactattg cagctcttac tgtcatcgct   1560

ggtgctggaa tggctgtggt gtctcctaaa cgcaaagaaa act                     1603
```

```
<210> SEQ ID NO 4
<211> LENGTH: 880
<212> TYPE: DNA
<213> ORGANISM: Streptococcus equi

<400> SEQUENCE: 4
```

```
tctgaggtta gtcgtacggc gactccaaga ttatcgcgtg atttaaaaaa tagattaagc     60

gatatagcca taagtggaga tgcctcatca gcccaaaaag ttcgaaatct tctaaaaggc    120

gcctctgttg ggatttaca ggcattattg agaggtcttg attcagcaag ggctgcgtat     180

ggtagagatg attattacaa tttattgatg cacctttcat cgatgttaaa tgataaacct    240

gatggggata gaagacaatt aagtttggct tcattacttg tagatgaaat tgaaaagcgg    300

attgctgatg gagataggta tgcaaaactt cttgaggcta aacttgcagc tattaaatct    360

caacaagaaa tgcttagaga aagagattcc caacttcgaa atctagagaa ggagaaagaa    420

caagagctca caaaagctaa agatgagcgt caagctctta ccgaatcatt caacaaaact    480

ttatcaagat caacaaaaga gtataataaa ctaaaaacag aacttgcaaa agaaaaagaa    540

aaagcagcta agatgactaa ggaattagca gataagctaa gcaatgctga agcaagtcgt    600

gataaagcct ttgcagtatc aaaagattta gcagataaac taagtagtgc tgaagcaagt    660

cgtgataaag cttttgcagt atcaaaagat ttagcagata aattggcagc taaaacagca    720

gaagctgaaa agttaatgga aaacgttggt agtctagacc gcttggtaga gtctgcaaaa    780

cgtgaaatgg ctcaaaaatt agcagaaatt gatcaattaa ctgctgataa ggctaaggct    840

gatgcagagc ttgcagctgc aaatgacacc attgcatcac                          880
```

-continued

<210> SEQ ID NO 5
<211> LENGTH: 294
<212> TYPE: PRT
<213> ORGANISM: Streptococcus equi

<400> SEQUENCE: 5

```
Asn Ser Glu Val Ser Arg Thr Ala Thr Pro Arg Leu Ser Arg Asp Leu
1               5                   10                  15

Lys Asn Arg Leu Ser Asp Ile Ala Ile Ser Gly Asp Ala Ser Ser Ala
            20                  25                  30

Gln Lys Val Arg Asn Leu Leu Lys Gly Ala Ser Val Gly Asp Leu Gln
        35                  40                  45

Ala Leu Leu Arg Gly Leu Asp Ser Ala Arg Ala Ala Tyr Gly Arg Asp
    50                  55                  60

Asp Tyr Tyr Asn Leu Leu Met His Leu Ser Ser Met Leu Asn Asp Lys
65                  70                  75                  80

Pro Asp Gly Asp Arg Arg Gln Leu Ser Leu Ala Ser Leu Leu Val Asp
                85                  90                  95

Glu Ile Glu Lys Arg Ile Ala Asp Gly Asp Arg Tyr Ala Lys Leu Leu
            100                 105                 110

Glu Ala Lys Leu Ala Ala Ile Lys Ser Gln Gln Glu Met Leu Arg Glu
        115                 120                 125

Arg Asp Ser Gln Leu Arg Asn Leu Glu Lys Glu Lys Glu Gln Glu Leu
    130                 135                 140

Thr Lys Ala Lys Asp Glu Arg Gln Ala Leu Thr Glu Ser Phe Asn Lys
145                 150                 155                 160

Thr Leu Ser Arg Ser Thr Lys Glu Tyr Asn Lys Leu Lys Thr Glu Leu
                165                 170                 175

Ala Lys Glu Lys Glu Lys Ala Ala Lys Met Thr Lys Glu Leu Ala Asp
            180                 185                 190

Lys Leu Ser Asn Ala Glu Ala Ser Arg Asp Lys Ala Phe Ala Val Ser
        195                 200                 205

Lys Asp Leu Ala Asp Lys Leu Ser Ser Ala Glu Ala Ser Arg Asp Lys
    210                 215                 220

Ala Phe Ala Val Ser Lys Asp Leu Ala Asp Lys Leu Ala Ala Lys Thr
225                 230                 235                 240

Ala Glu Ala Glu Lys Leu Met Glu Asn Val Gly Ser Leu Asp Arg Leu
                245                 250                 255

Val Glu Ser Ala Lys Arg Glu Met Ala Gln Lys Leu Ala Glu Ile Asp
            260                 265                 270

Gln Leu Thr Ala Asp Lys Ala Lys Ala Asp Ala Glu Leu Ala Ala Ala
        275                 280                 285

Asn Asp Thr Ile Ala Ser
    290
```

<210> SEQ ID NO 6
<211> LENGTH: 27
<212> TYPE: DNA
<213> ORGANISM: Streptococcus equi

<400> SEQUENCE: 6
gcggatccga actctgaggt tagtcgt 27

<210> SEQ ID NO 7
<211> LENGTH: 28

-continued

<212> TYPE: DNA
<213> ORGANISM: Streptococcus equi

<400> SEQUENCE: 7
gcggatccat agcttagttt tctttgcg 28

<210> SEQ ID NO 8
<211> LENGTH: 20
<212> TYPE: DNA
<213> ORGANISM: Streptococcus equi

<400> SEQUENCE: 8
tgcataaaga agttcctgtc 20

<210> SEQ ID NO 9
<211> LENGTH: 20
<212> TYPE: DNA
<213> ORGANISM: Streptococcus equi

<400> SEQUENCE: 9
gattcggtaa gagcttgacg 20

<210> SEQ ID NO 10
<211> LENGTH: 1889
<212> TYPE: DNA
<213> ORGANISM: Streptococcus equi

<400> SEQUENCE: 10

```
tacattcttg cttattaaat aaaaatgaca atgtactgca taaagaagtt cctgtcatta     60
aaataaaagt gccatgaggt tataatagta tggtaaaaca aaaaagtgtg cccataacgg    120
gtagagagga attgacatat gtttttgaga aataacaagc caaaatttag catcagaaaa    180
ctaagtgccg gtgcagcatc agtattagtt gcaacaagtg tgttgggagg gacaactgta    240
aaagcgaact ctgaggttag tcgtacggcg actccaagat tatcgcgtga tttaaaaaat    300
agattaagcg atatagccat aagtggagat gcctcatcag cccaaaaagt tcgaaatctt    360
ctaaaaggcg cctctgttgg ggatttacag gcattattga gaggtcttga ttcagcaagg    420
gctgcgtatg gtagagatga ttattacaat ttattgatgc acctttcatc gatgttaaat    480
gataaacctg atggggatag aagacaatta agtttggctt cattacttgt agatgaaatt    540
gaaaagcgga ttgctgatgg agataggtat gcaaaacttc ttgaggctaa acttgcagct    600
attaaatctc aacaagaaat gcttagagaa agagattccc aacttcgaaa tctagagaag    660
gagaaagaac aagagctcac aaaagctaaa gatgagcgtc aagctcttac cgaatcattc    720
aacaaaactt tatcaagatc aacaaaagag tataataaac taaaaacaga acttgcaaaa    780
gaaaaagaaa aagcagctaa gatgactaag gaattagcag ataagctaag caatgctgaa    840
gcaagtcgtg ataaagcctt tgcagtatca aaagatttag cagataaact aagtagtgct    900
gaagcaagtc gtgataaagc ttttgcagta tcaaaagatt tagcagataa attggcagct    960
aaaacagcag aagctgaaaa gttaatggaa aacgttggta gtctagaccg cttggtagag   1020
tctgcaaaac gtgaaatggc tcaaaaatta gcagaaattg atcaattaac tgctgataag   1080
gctaaggctg atgcagagct tgcagctgca aatgacacca ttgcatcact tcaaacagag   1140
ctagaaaaag ctaagacaga gcttgctgtt tcagagcgtt tgattgaatc aggcaaacgt   1200
gaaattgctg agctacaaaa acaaaaagat gcttctgata aggctttagt agaatcacaa   1260
gctaatgtag cagagcttga aaaacaaaaa gcagcatcag atgctaaggt agcagagctt   1320
```

-continued

```
gaaaaagaag ttgaagctgc taaagctgag gttgcagatc ttaaagcaca attagctaag   1380

aaagaagaag agcttgaagc cgttaagaag gaaaaagaag cgcttgaagc taagattgaa   1440

gagctcaaaa aagctcatgc tgaggaactt tcaaaactta aagaaatgct tgagaagaaa   1500

gaccatgcaa atgcagatct tcaagcagaa atcaatcgct tgaagcaaga gctagctgac   1560

aggattaagt cattgtcaca aggtggtcgt gcttcacaaa caaacccagg cactacaact   1620

gctaaagcag gtcaattgcc atctactggt gagtctgcta acccattctt cactattgca   1680

gctcttactg tcatcgctgg tgctggaatg gctgtggtgt ctcctaaacg caaagaaaac   1740

taagctattt cctctttccc caatggacaa tagccgaaat aatagagcga ctatcgttct   1800

aacacaaaag caacagtctc ctgtctgttg ctttttgtga tattagggct catcagtcta   1860

ggctaatggt tttctgcgct ttatctgca                                      1889
```

COMPOUNDS ENCODING THE PROTECTIVE M-LIKE PROTEIN OF *STREPTOCOCCUS EQUI* AND ASSAYS THEREFOR

This application claims priority to U.S. Provisional Patent Application No. 60/050,577, filed Jun. 24, 1997.

This invention was developed under a grant from the U.S. Government: USDA-NRICGP Number 95-01837, and therefore, the U.S. Government may have certain rights in this invention.

BACKGROUND OF THE INVENTION

The present invention relates generally to molecular compounds which encode the protective M-like protein of *Streptococcus equi* (SeM), the amino acid compound which is thereby encoded, and compositions of matter which incorporate either the encoding compounds or the cellular components for which they encode. For instance, vaccines which utilize the amino acid compounds or vectors and cell lines useful to make the amino acid compounds described herein are subjects of the present invention. The present invention provides methods to stimulate *S. equi*-specific immune response in horses. It also provides diagnostic assays for *Streptococcus equi.*

*Streptococcus equi,* a Lancefield group C streptococcus, causes strangles, a highly contagious disease of the nasopharynx and draining lymph nodes of Equidae. The 58 kDa antiphagocytic M-like protein (SeM) is a major virulence factor and protective antigen and functions by limiting deposition of C3b on the bacterial surface and by directly binding fibrinogen. Boschwitz and Timoney, 17 *Microbiol. Pathogenesis* 121 (1994) and Boschwitz and Timoney, 62 *Infect. Imnun.* 3515 (1994).

In the recent past, *S. equi* outbreaks on horse farms have been avoided and treated by quarantine of suspect animals; antiseptic handling of food, bedding and housing; and antibiotics when indicated. Vaccines comprising avirulent *S. equi* or fractions thereof have been described, but success rate has been low. U.S. Pat. No. 5,183,659 describes a vaccine which stimulated a nasopharyngeal antibody response in horses, but the vaccine had a limitation of many such vaccines, which is risk of reversion to virulence and occasional abcess development in vaccinated horses.

*S. equi* is shed in nasal discharges and pus from lymph nodes of affected animals. Routine laboratory detection of the bacterium involves bacteriologic culture of nasal swabs, nasal washes and pus from abscesses and is often difficult because of background contamination, small numbers of the organism, or the presence of *S. zooepidemicus* and other β-hemolytic streptococci. Completion of culture and identification usually takes 2 to 3 days, an excessively lengthy interval given the highly contagious nature of strangles and the need to quickly identify shedding horses so that they may be isolated in the early stages of an outbreak.

SUMMARY OF THE INVENTION

It is an object of the present invention to provide molecular compounds which encode SeM and compositions of matter which incorporate either the encoding compounds or the cellular components for which they encode.

It is therefore an object to provide vectors, cell lines and cell membrane preparations using the compounds disclosed.

It is yet another object to provide a method to provide assays for detection of *Streptococcus equi.*

Other objects and features of the present invention win be apparent from the following detailed description, examples and claims.

Definitions

As used herein, the following terms shall have the corresponding meaning set forth. All other terms are intended to have the meaning as understood commonly by those in the relevant field of art.

"Biological Sample" means nasal or oral mucus sample or blood sample.

"Transformation" and "transfection" mean to cause nucleic acid to enter a cell, whether or not the nucleic acid incorporates into the genome.

BRIEF DESCRIPTION OF THE DRAWINGS

The invention will be further described in conjunction with the accompanying drawings, in which:

FIG. 1 (SEQ ID NO:10) is the nucleotide and deduced amino acid sequence of SeM. Base and amino acid positions are shown on the left. Putative promoter and ribosomal binding sites (RBS) are boxed, and signal and membrane anchor sequences are shown in bold type. Repeats are underlined.

DETAILED DESCRIPTION OF THE INVENTION

Figure 2:
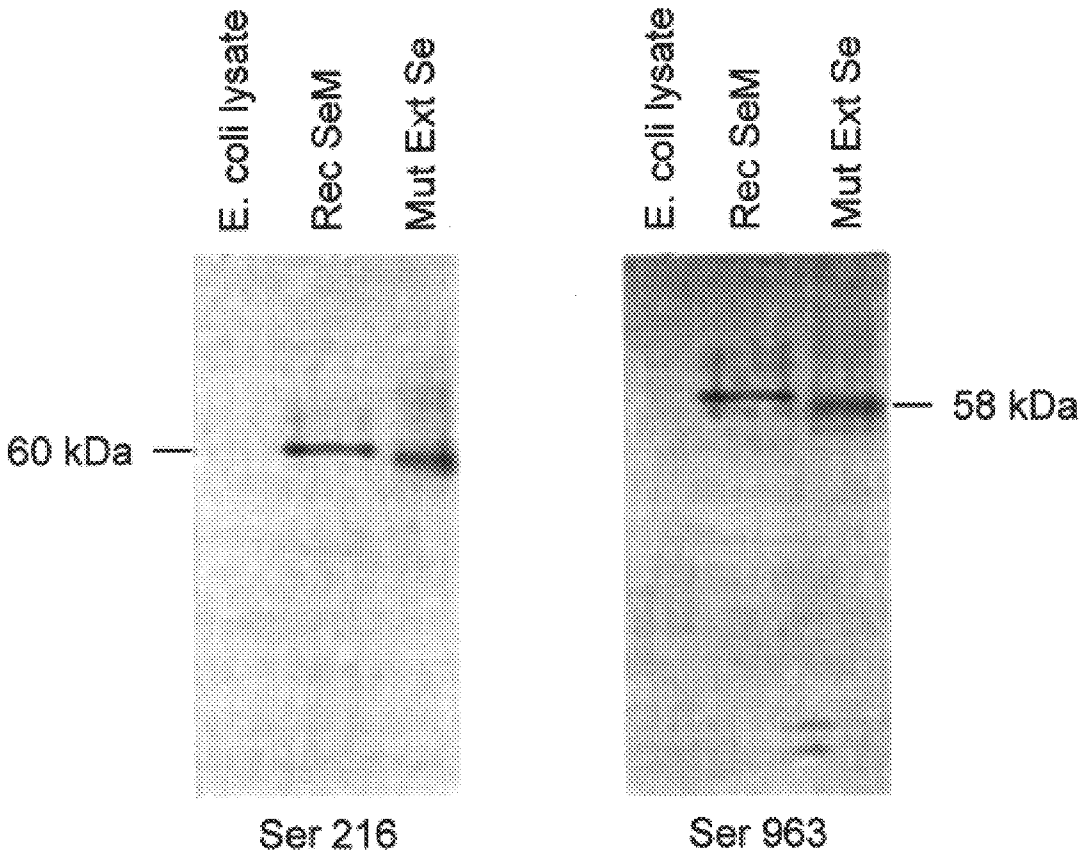
FIG. 2 is an immunoblot showing reactions of a lysate of *E. coli* BL21, SeM02 and a mutanolysin extract of *S. equi* with antisera 216 and 963 to SeM and recombinant SeM respectively.

The present invention provides nucleic acid compounds comprising a compound of the following sequence:

```
   1 AGCTTTCTGTCACCTGATGGTCCTTATCAAATACTGTAATTGATAACTTCAAACAGCCCT
  61 GTAGAGATTTTACTAACGACATAGTATCCATGCTAAGCGTCACCCCCTTCATAATCCTCA
 121 CGGTATCTTATTCTATCTTAAAATTTAAGAAAAGCAAGGATATGCACTTATAATGAAAAA
 181 ATAGACATAAAAAACAATAATATACATTCTTGCTTATTAAATAAAAATGACAATGTACTG
 241 CATAAAGAAGTTCCTGTCATTAAAATAAAAGTGCCATGAGGTTATAATAGTATGGTAAAA
 301 CAAAAAAGTGTGCCCATAACGGGTAGAGAGGAATTGACATATGTTTTTGAGAAATAACAA
 361 GCCAAAATTTAGCATCAGAAAACTAAGTGCCGGTGCAGCATCAGTATTAGTTGCAACAAG
 421 TGTGTTGGGAGGGACAACTGTAAAAGCGAACTCTGAGGTTAGTCGTACGGCGACTCCAAG
 481 ATTATCGCGTGATTTAAAAAATAGATTAAGCGATATAGCCATAAGTGGAGATGCCTCATC
 541 AGCCCAAAAAGTTCGAAATCTTCTAAAAGGCGCCTCTGTTGGGGATTTACAGGCATTATT
 601 GAGAGGTCTTGATTCAGCAAGGGCTGCGTATGGTAGAGATGATTATTACAATTTATTGAT
 661 GCACCTTTCATCGATGTTAAATGATAAACCTGATGGGGATAGAAGACAATTAAGTTTGGC
 721 TTCATTACTTGTAGATGAAATTGAAAAGCGGATTGCTGATGGAGATAGGTATGCAAAACT
 781 TCTTGAGGCTAAACTTGCAGCTATTAAATCTCAACAAGAAATGCTTAGAGAAAGAGATTC
 841 CCAACTTCGAAATCTAGAGAAGGAGAAAGAACAAGAGCTCACAAAAGCTAAAGATGAGCG
 901 TCAAGCTCTTACCGAATCATTCAACAAAACTTTATCAAGATCAACAAAAGAGTATAATAA
 961 ACTAAAAACAGAACTTGCAAAAGAAAAAGAAAAAGCAGCTAAGATGACTAAGGAATTAGC
1021 AGATAAGCTAAGCAATGCTGAAGCAAGTCGTGATAAAGCCTTTGCAGTATCAAAAGATTT
1081 AGCAGATAAACTAAGTAGTGCTGAAGCAAGTCGTGATAAAGCTTTTGCAGTATCAAAAGA
1141 TTTAGCAGATAAATTGGCAGCTAAAACAGCAGAAGCTGAAAAGTTAATGGAAAACGTTGG
1201 TAGTCTAGACCGCTTGGTAGAGTCTGCAAAACGTGAAATGGCTCAAAAATTAGCAGAAAT
1261 TGATCAATTAACTGCTGATAAGGCTAAGGCTGATGCAGAGCTTGCAGCTGCAAATGACAC
1321 CATTGCATCACTTCAAACAGAGCTAGAAAAAGCTAAGACAGAGCTTGCTGTTTCAGAGCG
1381 TTTGATTGAATCAGGCAAACGTGAAATTGCTGAGCTACAAAAACAAAAAGATGCTTCTGA
1441 TAAGGCTTTAGTAGAATCACAAGCTAATGTAGCAGAGCTTGAAAAACAAAAAGCAGCATC
1501 AGATGCTAAGGTAGCAGAGCTTGAAAAAGAAGTTGAAGCTGCTAAAGCTGAGGTTGCAGA
1561 TCTTAAAGCACAATTAGCTAAGAAAGAAGAAGAGCTTGAAGCCGTTAAGAAGGAAAAAGA
1621 AGCGCTTGAAGCTAAGATTGAAGAGCTCAAAAAAGCTCATGCTGAGGAACTTTCAAAACT
1681 TAAAGAAATGCTTGAGAAGAAAGACCATGCAAATGCAGATCTTCAAGCAGAAATCAATCG
1741 CTTGAAGCAAGAGCTAGCTGACAGGATTAAGTCATTGTCACAAGGTGGTCGTGCTTCACA
1801 AACAAACCCAGGCACTACAACTGCTAAAGCAGGTCAATTGCCATCTACTGGTGAGTCTGC
1861 TAACCCATTCTTCACTATTGCAGCTCTTACTGTCATCGCTGGTGCTGGAATGGCTGTGGT
1921 GTCTCCTAAACGCAAAGAAAACTAAGCTATTTCCTCTTTCCCCAATGGACAATAGCCGAA
1981 ATAATAGAGCGACTATCGTTCTAACACAAAAGCAACAGTCTCCTGTCTGTTGCTTTTTGT
2041 GATATTAGGGCTCATCAGTCTAGGCTAATGGTTTTCTGCGCTTTATCTGCA
```

[SEQ ID NO. 1 (M-protein (SeM) gene of *S. equi*)]. The open reading frame starts at 341 and continues to base 1934. Preferably, the compound is SEQ ID NO 1. However, also provided are compounds which are complementary to SEQ ID NO 1 or complementary to portions of SEQ ID NO 1. A preferred portion of SEQ ID NO 1 is that described above as base number 341 to 1943, inclusive (SEQ ID NO 3). Moreover, the compound defined by bases number 452 through approximately 1331 are also preferred (SEQ ID NO 4).

As skilled artisans can appreciate, the DNA compounds exemplified above can readily instruct one as to useful, complementary RNA sequences. Any such RNA sequences are also considered within the scope of the present invention.

In the present disclosure, this group of DNA and RNA compounds are termed "nucleic acid compounds".

Moreover, cells transfected with a (or multiple copies of a) nucleic acid compound of the present invention are provided. Preferred is a cell transfected with SEQ ID NO 1 or a portion thereof. Such cells may be prokaryotic or eukaryotic. Preferred cells include: *E. coli, S. cerevisiae,* and Salmonella spp. Also provided are vectors transfected with a (or multiple copies of a) nucleic acid compound of the present invention. Preferred vectors include pox viruses, adenoviruses or other viral vectors.

The nucleic acid compounds may be obtained by PCR using primers as is skill of the art, or from Gen Bank, accession number U73162. Vectors and cell lines can also be obtained as is skill of the art.

Moreover, also provided is the amino acid compound:

```
         5         10         15         20         25         30

  1M F L R N N K P K F S I R K L S A G A A S V L V A T S V L G
 31G T T V K A N S E V S R T A T P R L S R D L K N R L S D I A
 61I S G D A S S A Q K V R N L L K G A S V G D L Q A L L R G L
 91D S A R A A Y G R D D Y Y N L L M H L S S M L N D K P D G D
121R R Q L S L A S L L V D E I E K R I A D G D R Y A K L L E A
151K L A A I K S Q Q E M L R E R D S Q L R N L E K E K E Q E L
181T K A K D E R Q A L T E S F N K T L S R S T K E Y N K L K T
211E L A K E K E K A A K M T K E L A D K L S N A E A S R D K A
241F A V S K D L A D K L S S A E A S R D K A F A V S K D L A D
271K L A A K T A E A E K L M E N V G S L D R L V E S A K R E M
301A Q K L A E I D Q L T A D K A K A D A E L A A A N D T I A S
331L Q T E L E K A K T E L A V S E R L I E S G K R E I A E L Q
361K Q K D A S D K A L V E S Q A N V A E L E K Q K A A S D A K
391V A E L E K E V E A A K A E V A D L K A Q L A K K E E E L E
421A V K K E K E A L E A K I E E L K K A H A E E L S K L K E M
451L E K K D H A N A D L Q A E I N R L K Q E L A D R I K S L S
481Q G G R A S Q T N P G T T T A K A G Q L P S T G E S A N P F
511F T I A A L T V I A G A G M A V V S P K R K E N
```

which is SEQ ID NO 2. The present invention also includes portions of the above sequence. The most preferred portion of the above sequence is: residues 37 to 330 (SEQ ID NO 5) however, one skilled in the art recognizes that any especially antigenic portion is commercially significant, and is included in the scope of the present invention.

The amino acid compounds can be obtained either by overexpression and purification in microorganisms, or, in some cases, by conventional peptide synthesis.

Therefore, a vaccine for *S. equi* is provided by the present invention. A vaccine which is administered intranasally or orally is a preferred embodiment. A vaccine of the present invention can comprise the entire SEQ ID NO 2, or portions thereof.

The vaccines of the present invention can be of any pharmaceutically-acceptable formulation. For example, SEQ ID NO 5 can be incorporated into bilayer vesicles (liposomes), in an aqueous medium according to known procedures, such as that described by Debs et al., 265 *J. Biol. Chem.* 10189 (1990). Any available carrier or liposome-forming lipid may be utilized in any formulation which delivers SeM antigen, for example, poly-DL-Lactide-co-glycolide may be utilized in an intranasal spray formulation which comprises SEQ ID NO 5. Formulations which include adjuvants which enhance the delivery of antigen to the mucosa, such as small amounts of the Bsubunit of the cholera toxin are also within the scope of the present invention.

The present invention also provides methods to stimulate a *S. equi*-specific immune response in horses comprising administering a compound of SEQ ID NO 2 or portions thereof. Introduction of the antigen nasally or orally is preferred.

Lastly, the present invention provides methods to determine the presence of *S. equi* in horses via polymerase chain reaction. The polymerase chain reaction diagnostic assay of the present invention can be accomplished according to known methods so long as primers for the sequence herein disclosed are used as some of the starting materials. Methods for PCR can be found in many journals and books, for instance, the PCR diagnostic methods can be accomplished according to *Techniques in PCR, PCR, Current Protocols in Molecular Biology or Maniatis.* As skilled artisans are aware, preferred primers are those which are at least 50% GC content, ideally 19 to 23 base pairs in length, and are not capable of annealing to duplicate sections of the target DNA.

EXAMPLES

Example 1

Cloning, Sequencing and Expression of SeM

Chromosomal DNA of *S. equi* CF32 was partially digested with Tsp 5091 (New England Biolabs Inc., Beverly Mass.) and 3–8 kb fragments ligated to λ ZAPII digested with EcoRI (Stratagene, LaJolla, Calif.). After packaging (Gigapack II) (Stratagene, LaJolla, Calif.) and transfection into *E. coli* XLI-Blue MRF' (Stratagene, LaJolla, Calif.) , the library was plated, amplified and stored at −70° C. in 7% DMSO. The library was screened on duplicate nitrocellulose discs by using rabbit 216 antiserum (1:4000 dilution) to the acid extracted 41 kDa fragment of SeM. Several reactive plaques were screened until all plaques gave a positive signal. Proteins in these phage lysates were separated by SDS PAGE and immunoblotted with serum 216. A plasmid containing a 3.5 kb fragment encoding SeM was excised from a positive phage and the resulting plasmid designated pSeM01. Nucleotide sequencing was performed on HindIII, Pvu II and Hind III-Pvu II fragments of the *S. equi* insert in pSK by automated cycle sequencing. Sequences were aligned and connected by DNASIS (Hitachi Software Engineering America, Ltd., San Diego, Calif.). SeM without its signal sequence was subcloned into the Bam H1 site of the pET15b (Novagen, Madison, Wis.) expression vector using the polymerase chain reaction (PCR) with pSeM01 as template and primers SeM-F (gcggatcCGAACTCTGAGGTTAGTCGT) (SEQ ID NO 6) and SeM-R (gcggatccATAGCTTAGTTTTCTTTGCG) (SEQ ID NO 7). The resulting plasmid was designated pSeM02 and transformed into *E. coli* BL21 (DE3). Recombinant SeM was isolated from a lysate of BL21 by affinity chromatography on His-Bind Resin (Novagen, Madison, Wis.).

Analysis of the connected sequences revealed the presence of one open reading frame of 1605 nucleotides encoding the seM gene (FIG. 1). Translation of seM revealed a basic (CH+4.5) preprotein of 535 amino acids of calculated molecular mass 58,251 and pI of 8.67. N terminal amino acid sequence (residues 37–52) was identical to that obtained by direct microsequencing of the 41 kDa SeM fragment purified from an acid extract of *S. equi.* The predicted amino acid sequence exhibits features typical of streptococcal surface proteins. The signal sequence is 36 residues. The N terminus of the mature protein has a net positive charge. The anchor membrane spanning region and charged tail sequences are similar to those of other group A and C streptococcal sequences. Two direct repeats (21 residues) are located between residues 226 and 267. Other shorter direct repeats varying in length from 3 to 6 residues occur in the carboxy terminal half of the molecule. Analysis of the secondary structure of the translated protein shows an extensive region of alpha helix extendnng approximately from residue 120 to 480. The secondary structure prediction shows turns in the vicinity of residues 120 and 480 to 500.

Example 2

Amino Acid Sequence Determination

Acid extracted SeM (2 mg) purified as described in Example 3 was loaded onto a 2 cm wide slot on a 1.5 mm thick acrylamide (9%) gel for preparative SDS PAGE. The gel was prerun with 0.1 mM thioglycolic acid for 40 mins at 100 V before loading the protein. Following electrophoresis, and electrophoretic transfer to Immobilon P (Millipore), the major 41 and 46 kDa fragments of SeM were identified by staining for 1 min. with 0.025% Coomassie blue in 40% methanol and 5% glacial acetic acid followed by destaining for 2 min in 30% methanol and 5% glacial acetic acid. The 41 kDa band was excised and microsequence analysis performed on a model 477A pulse liquid phase sequencer (Applied Bio Systems) at the University of Kentucky Macromolecular Synthesis Laboratory.

Example 3

Protein Extraction

M-like protein was extracted from an overnight culture (18 h) of *S. equi* by hot acid extraction (Lancefield and Perlmann. 96 *J. Exp. Med.* 71 (1952) and adsorbed to a column of hydroxyapatite in 10 mM phosphate buffer pH 7.2. The M-like proteins were eluted in 0.2 M Na2HPO4, desalted on Sephadex G25 and lyophilized. The pellet was dissolved in 25% acetonitrile+0.5% trifluoroacetic acid and loaded on a phenyl RP reverse phase column (Bio-Rad, San Francisco Calif.) connected to a Waters 650 protein purification system (Waters, Marlborough, Mass.). Protein was eluted using a linear gradient of 25–65% acetonitrile+0.5% TFA. A dot immunoblot on cellulose nitrate using SeM specific rabbit antiserum was used to screen peaks. The peak containing SeM protein eluted at a concentration of approximately 42% acetonitrile. Positive peaks from several runs were pooled and further purified on the same column. Purified protein was lyophilized, resuspended in PBS and stored in aliquots at −20° C. Mutanolysin extracts of *S. equi* strains were performed as described previously (Galán and Timoney, 26 *J. Clin. Microbiol.* 1142 (1988).

Example 4

Antisera

Antiserum was raised against SeM purified by a combination of hydroxyapatite and reverse-phase chromatography. A New Zealand white rabbit (216) was injected subcutaneously with 50 μg SeM in complete Freund's adjuvant followed at 3 week intervals by 2 similar doses emulsified in incomplete Freund's adjuvant. Serum was harvested at 8 weeks. Rabbit 963 was similarly hyperimmunized with recombinant SeM from *E. coli* sonicate. Rabbit Ec was immunized with a lysate of *E. coli* NovaBlue containing plasmid pT7 Blue without an insert. Adult ICR mice were immunized with 25 μg SeM purified from *E. coli* sonicate by HIS-Tag chromatography. Purified SeM (25 μg) was mixed with 5 μg mycolic dipeptide (MDP) and alhydrogel (30%) and administered subcutaneously in a dose volume of 100 ml. Two subcutaneous booster doses containing 25 μg SeM but no MDP were administered 10 and 20 days later. Mice were bled at 28 days. All antisera were stored at −70° C. until used.

Example 5

Immunoblotting

Proteins in streptococcal extracts or purified from *E. coli* sonicate were separated by SDS-10% polyacrylamide gel electrophoresis (PAGE) and electroblotted to a sheet of nitrocellulose and incubated in the appropriate antiserum diluted 1:200 in PBS and then in peroxidase-conjugated protein G (1:4000). Reactive bands were visualized by using 4-chloro-1-naphthol (0.5 mg/ml) as substrate.

Figure 3:
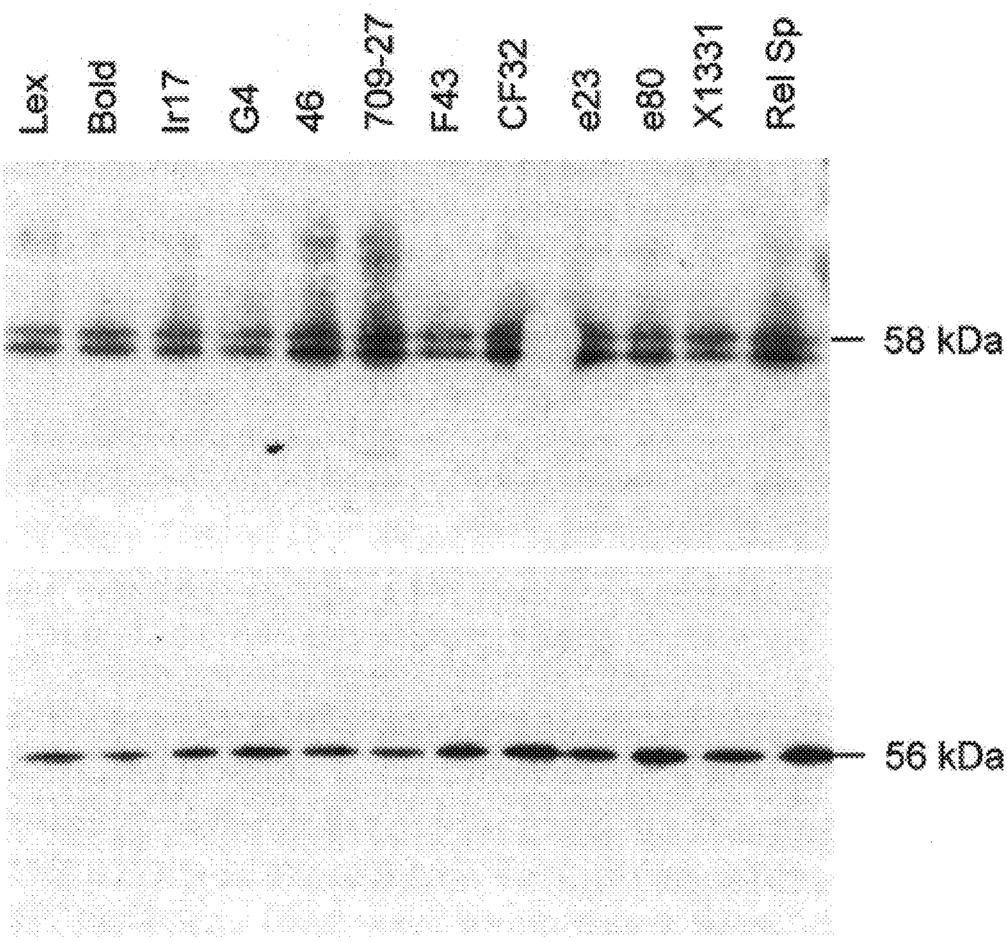
FIG. 3 is an immunoblot showing the reactions of mutanolysin extracts of a series of temporally and geographically separated isolates of *S. equi* with antisera to recombinant SeM. Estimated molecular masses are shown to the right of the figure.

Rabbit 963 antiserum to recSeM reacted with a 58 kDa protein in a mutanolysin extract of *S. equi* and with a slightly larger 60 kDa protein expressed by *E. coli* BL21 containing pSeM02 (FIG. 2). The same protein bands were recognized by rabbit 216 antiserum to the 41 kDa fragment of SeM. FIG. 3 shows the immunoblot profiles of mutanolysin extracts of a series of *S. equi* isolates collected at different times in the US and Europe. Antiserum to recSeM recognized two protein bands of 58 and 56 kDa in all the extracts.

Example 6

ELISA

An acid extracted fragment (41 kDa) of SeM purified by preparative electrophoresis on agarose was used to coat wells (2.5 mg/well) of polystyrene ELISA plates (Costar, 25880, Corning Glass Company, Corning N.Y.). After washing and blocking in 0.1 M phosphate buffered saline (PBS) containing 0.05 Tween 20 and 1% bovine serum albumin, mouse or rabbit sera diluted 1:80 and 1:200 respectively in PBS were added in triplicate to the wells (100 ml/well). After incubation for 3 hours at 37° C., bound IgG was detected with either peroxidase conjugated protein G (1:4000) or rabbit anti-mouse IgG followed by O-phenylene diamine (0.0001 mM) solution. Mean OD values of triplicate readings were blanked against wells containing antigen and PBS.

Example 7

Opsonic Assay

Equine neutrophils were separated from freshly collected heparinized horse blood with a discontinuous Percoll gradient Pycock et al., 42 *Res. Vet. Sci.* 411 (1987). Neutrophils from 7 ml of blood were suspended in RPM1 medium (Gibco, Grand Island, N.Y.) and 80 ml aliquots (6×105 cells) added in triplicate to wells of a 24 well cell culture cluster (Costar, Cambridge, Mass.). Each well contained a circular glass coverslip (12 mm diameter). The cell cluster was incubated for 2 h at 37° C. in 5% CO2 and the cells washed once with PBS to remove non-adherent neutrophils. The test organisms (*S. equi* CF32 and *S. zooepidemicus* W60) were grown overnight at 37 C. in THB with 0.2% yeast extract to an OD of 0.6. Twenty ml of culture was added to 25 ml serum and 450 ml RPMI added. After the plate was gently shaken for 30 minutes at 37 C. the coverslips were washed once with PBS (pH 7.2) fixed in 10% formalin and stained with Giemsa The numbers of neutrophils with associated streptococci per 100 cells were then counted for each serum and expressed as a percentage. All assays were performed in triplicate. The differences in the opsonic activities of immune and control sera were evaluated statistically by a Student t-test (Unpaired Observations) based on the means of three experiments.

Sera from mice immunized with purified recombinant SeM showed 15 times greater ($p<0.01$) opsonic activity for *S. equi* than non-immune mouse sera. These sera also showed strong antibody responses by ELISA to the 41 kDa fragment of SeM (Example 6).

Example 8

Fibrinogen Binding Assay

Equine fibrinogen (0.5 mg/well) was bound to wells of 96 well polystyrene ELISA plates (Costar). After washing and blocking, recombinant SeM (0.4 mg/well) was added in triplicate to separate wells and incubated for 2 hours at 37 C. After washing, 1:80 dilutions of rabbit antisera to the 41 kDa fragment of SeM was added to the appropriate wells and incubated at 37 C. for 2 hours. Control wells consisted of wells from which fibrinogen was omitted and wells treated with sera from the same rabbits before immunization. Amounts of specific rabbit antibody that bound to SeM fixed to fibrinogen were detected as described under ELISA.

SeM showed strong binding to equine fibrinogen immobilized on wells of ELISA plates. Mean ELISA value (±SD) for SeM bound to fibrinogen after correction for non-specific binding of the protein to blocked well surfaces was 0.9±0.1. The corrected value was 0.1±0.1 when preimmune sera were used to assay for binding of the streptococcal protein.

Example 9

Nucleotide Sequence Accession Numbers

The Gen Bank accession number for the nucleotide sequence of seM is U73162.

Example 10

Homologies

With the exception of signal and membrane anchor sequences, no homology of SeM with group A or G M protein sequences in the GenBank database was detected. SeM showed some homology between its signal (39% identity) and membrane anchor (66% identity) sequences with those in the database.

Example 11

Presence of SeM-binding Antibodies in Convalescent Horses

Figure 4:
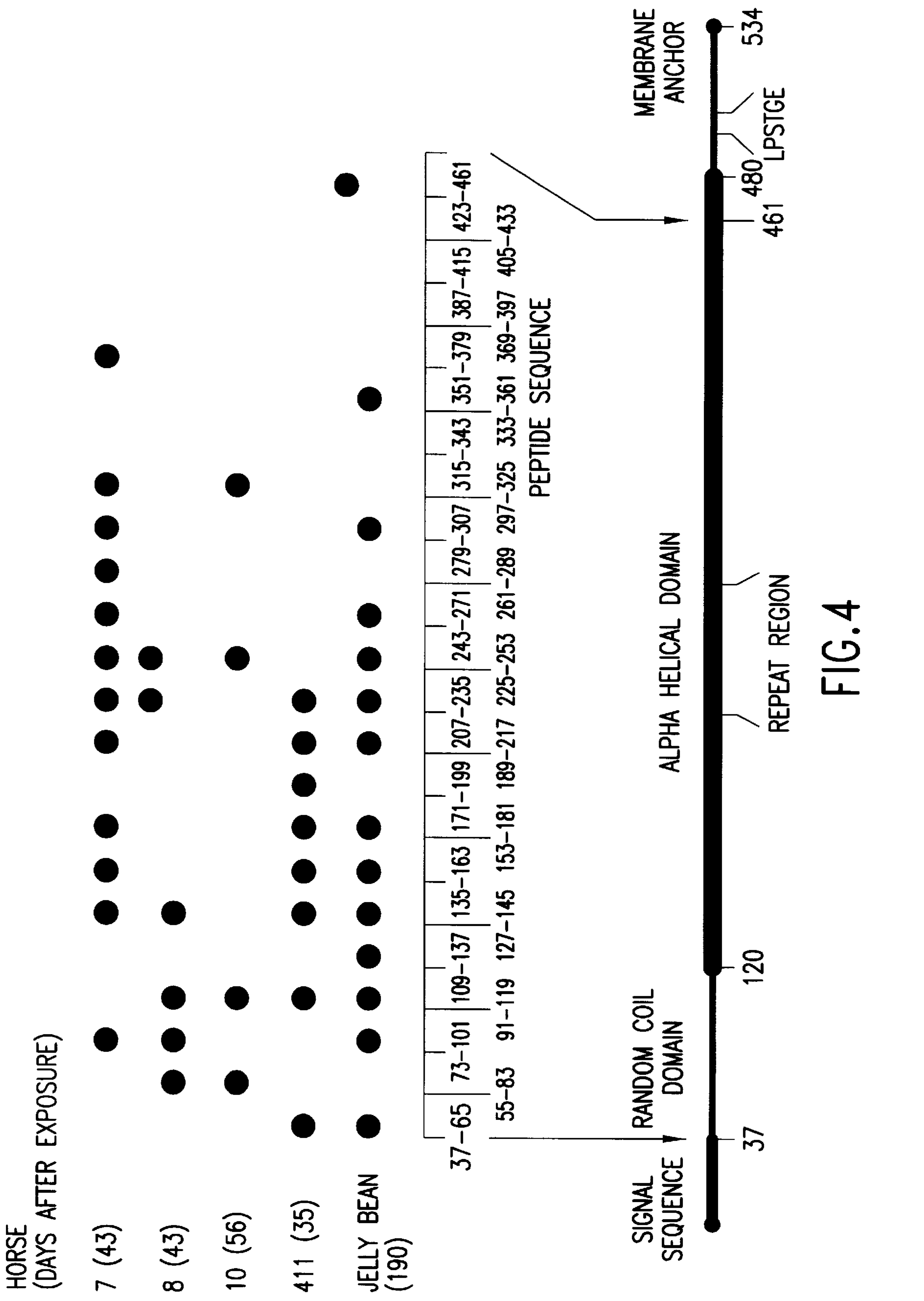
FIG. 4 is an immunoblot showing linear epitopes recognized by IgA in nasal washes of convalescent (8 weeks) horses.
Figure 5:
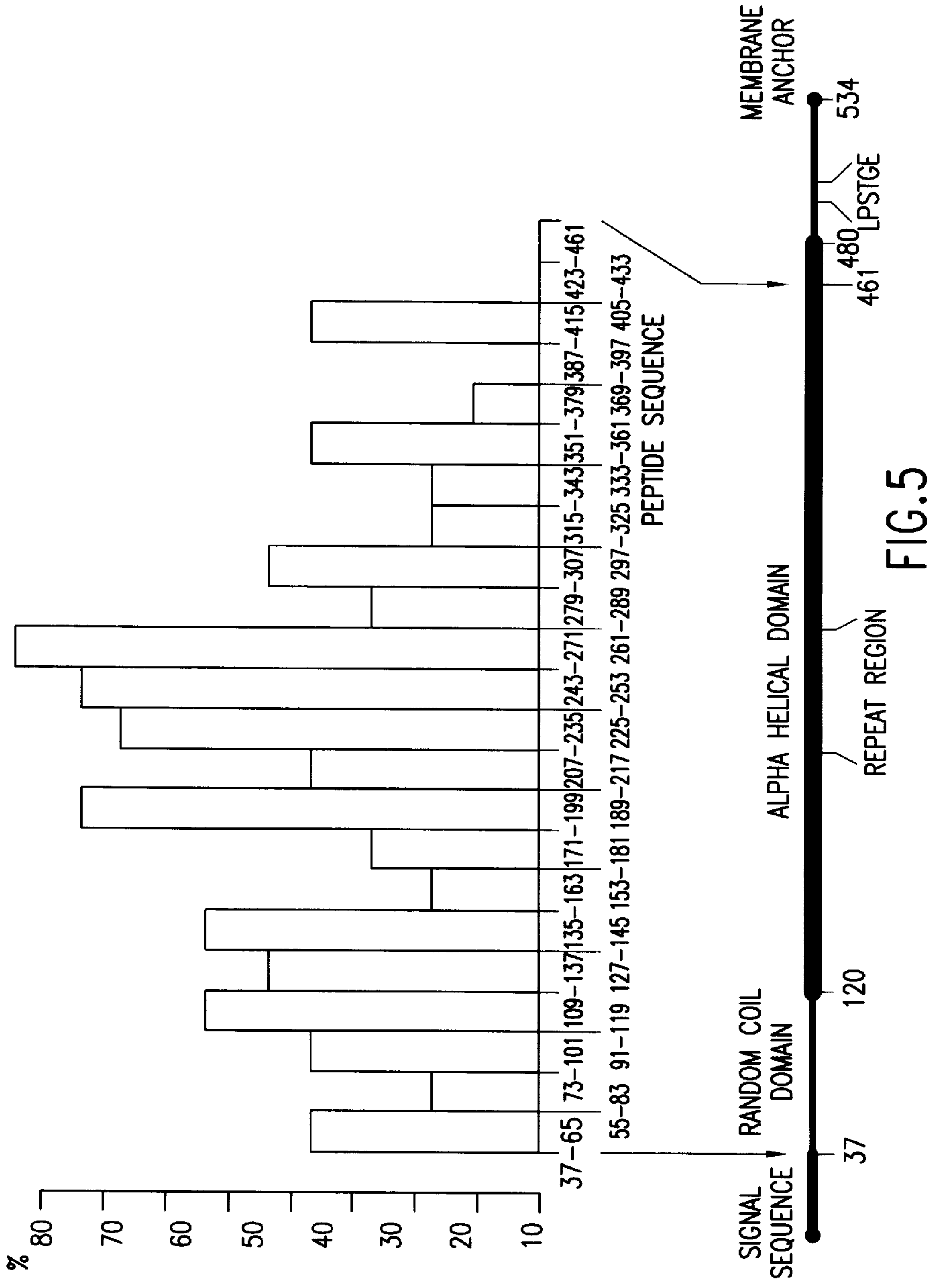
FIG. 5 is graph illustrating the regions of SeM reactive with antibodies in horse sera taken 8 weeks after recovery from strangles.

Regions of SeM reactive with antibodies in horse sera taken 8 weeks after recovery from strangles are shown in FIG. 3. Most horses showed reponses to epitopes on the central region of SeM (residues 170 to 270). Responses of individual horses to the N terminal third and carboxy terminal regions of SeM were much more variable. No horse responded to peptide 151–166 alone. Linear epitopes recognized by IgA in convalescent (8 weeks) nasal washes are found on the same region reactive with serum antibody (FIG. 4). Multiple epitopes are targeted and, as in the case of serum antibodies, there is considerable variation in the responses of individual horses.

Example 12

Immunizations of Non-exposed Yearling Ponies

Two groups of 3 yearling Welsh ponies were immunized with microencapsulated recombinant fusion peptide of the M-protein (SeM, amino acids 231–330) produced in *E. coli* BL21 and with a microencapsulated extract of the host *E. coli* alone. Encapsulated protein (100 μg) was sprayed into each nostril on day 1 using a nasal atomizer. Booster doses of 150 and 350 μg were given on days 7 and 42, respectively. Serum and nasal washes were collected at days 1, 7, 21 and 42 and assayed for SeM-specific IgG in serum and IgA in nasal washes, Specific mucosal IgA responses to SeM were evident at day 21 in 2 of the 3 ponies and in all ponies at day 49. None of the 3 control ponies immunized with *E. coli* extract alone responded to SeM. No serum antibody responses were detected in any pony. These studies demonstrate the feasibility of selectively-inducing specific mucosal antibody responses in horses by using a microencapsulated streptococcal peptide.

Example 13

PCR Diagnostic Assay

Nasal swabs (Precision Dynamic Corp. San Fernando, Calif.; Culturette, Baxter Healthcare Corp., Deerfield, Ill.) were collected from affected and exposed in-contact horses 1 to 5 days after clinical diagnosis of strangles on farms A, B, C, and D. Some horses were sampled more than once over the following 3 weeks. Nasal washes were collected from horses at UK farm 15 and 85 days following commingling exposure to 2 horses with clinical strangles. All these horses developed strangles within 17 days of commingling exposure. Nasal washes were collected by instilling 50 ml phosphate buffered saline (pH 7.2) via a 8 mm diameter latex tube inserted 15 cm into the nostril and collecting the fluid that drained out. The fluid was centrifuged at 3000 g and the pelleted debris separated for culture and PCR. Swabs and nasal wash pellets were cultured on Columbia CNA horse blood agar and incubated for 18 hours at 37° C. Beta hemolytic colonies were subcultured and their fermentation behavior tested in lactose, sorbitol and trehalose broths. Mucoid beta-hemolytic colonies that did not ferment any of these sugars were identified as *S. equi.*

DNA for PCR from nasal swabs and washes was prepared as follows: Swab tips were placed in 300 μl of sterile water, vortexed, the tips removed and the fluid centrifuged at 14,000 g for 10 minutes. The sediments were resuspended in 20 μl of K-buffer (1× Gen Amp Buffer II, Perkin Elmer, 0.5% Tween 20, 100 μg/ml Proteinase K). Nasal wash pellets were suspended in an equal volume of K-buffer. The suspensions were incubated for 30 minutes at 55° C., boiled for 5 minutes and then centrifuged for 5 minutes at 14,000 g. The reaction mix for PCR in a total volume of 30 μl was prepared in Gen Amp Buffer II and contained 2 mM $MgCl_2$, 0.2 mM dNTP, 0.5 units Taq polymerase, 0.25 μM SeM6 and SeM7 primers, and 2–5 μl sample. The primer sequences were 5'-TGCATAAAGAAGTTCCTGTC (SeM7-forward (bases 239–258) SEQ ID NO 8) and 5'-GATTCGGTAAGAGCTTGACG (SeM reverse(bases 899–918) SEQ ID NO 9). Mineral oil (30 μl) was added to seal the reaction mix. Cycling was performed as follows: –92° C. for 2 minutes; 92° C. for 1 minute; 58° C. for 1 minute; 72° C. for 1 minute (30 times); 72° C. for 5 minutes; 4° C. final. The PCR products were separated by ethidium bromide agarose gel electrophoresis. The SeM fragment amplified with primers SeM6 and 7 was 679 bp.

The PCR detected a 679 bp DNA fragment in 37 specimens including 14 of 15 that were positive by culture. The sensitivity of PCR appears to be much greater than culture.

Although the present invention has been fully described, it is to be noted that various changes and modifications are apparent to those skilled in the art Such changes and modifications are to be understood as included within the scope of the present invention as defined by the appended claims.

What is claimed is:

1. An isolated polypeptide from horse streptococcal comprising SEQ ID NO:2.

2. An isolated polypeptide from horse streptococcal comprising SEQ ID NO:5.

3. A composition comprising the polypeptide of claim 1 incorporated into a liposome.

4. A composition comprising the polypeptide of claim 3 further comprising the B-subunit of the cholera toxin.

5. A composition comprising the polypeptide of claim 2 incorporated into a liposome.

6. A composition comprising the polypeptide of claim 5 further comprising the B-subunit of Cholera Toxin.

* * * * *